United States Patent [19]

Döring

[11] Patent Number: 4,778,997

[45] Date of Patent: Oct. 18, 1988

[54] PROCESS AND DEVICE FOR DEPICTING THE DISTRIBUTION OF HIGH ACTIVITIES OF RADIOACTIVE SUBSTANCES

[76] Inventor: Volker Döring, Oberhofer Str. 32, D-2800 Bremen, Fed. Rep. of Germany

[21] Appl. No.: 772,420

[22] Filed: Sep. 4, 1985

[30] Foreign Application Priority Data

Sep. 8, 1984 [DE] Fed. Rep. of Germany ....... 3433109

[51] Int. Cl.⁴ .................. G01T 1/164; G21K 1/04
[52] U.S. Cl. .................. 250/363 S; 378/149; 378/150
[58] Field of Search .......... 250/363 SH, 363 R, 505.1, 250/515.1, 363 SR; 378/149, 150

[56] References Cited

U.S. PATENT DOCUMENTS 4,348,591  9/1982  Wunderlich .................. 250/363 R

FOREIGN PATENT DOCUMENTS 102184  8/1979  Japan .................. 250/363 SH
223081  12/1983  Japan .................. 250/363 SH

*Primary Examiner*—Carolyn E. Fields
*Attorney, Agent, or Firm*—Wegner & Bretschneider

[57] ABSTRACT

Process for depicting the distribution of high activities of radioactive substances by means of a whole-body scintigraphic device having a camera or the like, such as a gamma camera or scanner, characterized in that the radiation incident upon the camera is partially shielded against as a function of its intensity in order to optimize the counting rate, as well as a device for implementing such a process.

20 Claims, 3 Drawing Sheets

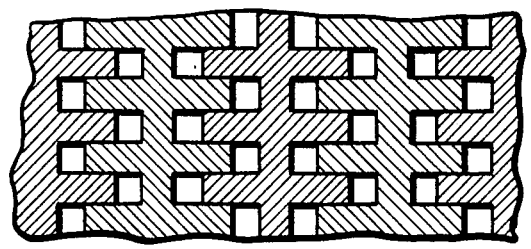
Fig.4
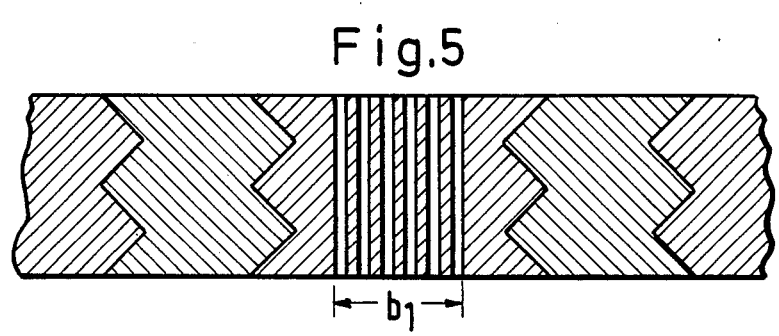
Fig.5
Fig.6
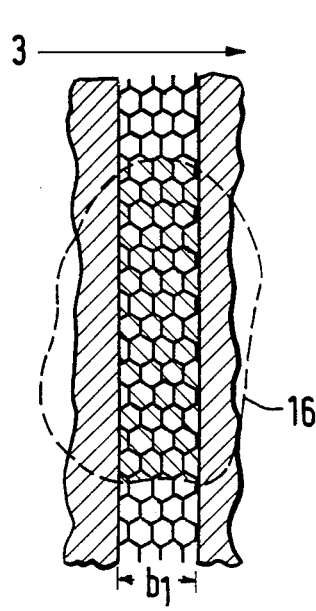
Fig.7
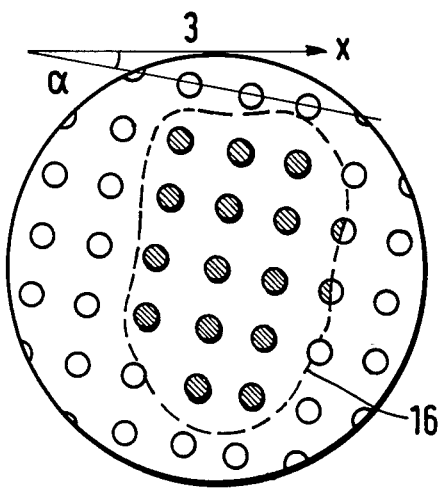

PROCESS AND DEVICE FOR DEPICTING THE DISTRIBUTION OF HIGH ACTIVITIES OF RADIOACTIVE SUBSTANCES

BACKGROUND OF THE INVENTION

The invention concerns a process and a device for depicting the distribution of high activities of radioactive substances as is used in the diagnostic technique of whole-body scintigraphy. The subject of the invention concerns depicting the distribution of high activities of radioactive substances using a whole-body scintigraphic device having a camera or the like, such as a gamma camera or scanner.

To depict the distribution of radioactive substances in bodies, especially in nuclear-medicine diagnostics for survey photographs of the entire patient (whole-body scintigraphy), gamma cameras having a whole-body attachment, or gamma cameras specially designed as a whole-body device, are preferentially used. Here the collimated sensor-head is generally moved in one or more adjacent paths parallel to the patient's longitudinal axis. A difficulty with such processes and devices is that, in the case of distributions of high activities, counting-rate errors may occur owing to "pile-ups" and dead-time effects, just as with the use of scanners whereby the object is scanned line by line in one plane -- the focal plane -- by a probe provided with a focussing collimator. These "pile-ups" and dead-time effects cause an erroneous depiction of the distribution of radioactive substances.

The underlying problem of the invention is to create a process and a device of the aforementioned type whereby counting-rate errors of the aforedescribed type are avoided.

Using a process of the aforementioned type, the invention solves this problem by partially shielding the whole-body scintigraphic device from radiation incident upon the device as a function of the radiation intensity in order to optimize the counting rate. The device according to this invention provides features allowing for partial shielding of the whole-body scintigraphic camera as a function of the intensity of radiation incident upon the device.

Especially preferred embodiments of the process and of the device according to the invention are objects of the subclaims.

The invention is based on the surprising perception that the described disadvantages of the known processes and devices can be eliminated, otherwise than in the prior art, by optimizing the counting rate from photograph to photograph each time by partial shielding against the high-activity radiation incident upon an optimal region of the scintigraphic device. By contrast, a collimator, known from DE-OS No. 27 31 629, for generating tomographic sectional images, undertakes to uniformize the sensitivity over the entire field of view of the camera by partially providing the latter with shielding material, no thought being given to any adaptation, varying from photograph to photograph, of the counting rate to an optimal region. The DE-OS No. 0 083 756 pertains to a collimator with adjustable aperture, a collimator which in the case of processes and devices of the generic type would likewise not afford the desired counting-rate optimization. Known from U.S. Pat. No. 4,012,636 is a diaphragm that is used to generate the whole-body measuring field and to prevent so-called "zipper errors" when adjacent imaging paths overlap or when there are gaps between them, though here too the counting-rate reduction, proposed according to the invention, would remain unaddressed. Finally, the WO-OS No. 82/00897 shows a multitube collimator for a scintillation camera, a collimator in which the sensitivity and resolution can be influenced by modifying the collimator, though here too the principle of the counting-rate optimization according to the invention would remain unaddressed. Rather what this involves is the change in position between high resolution and high sensitivity, without having to change the collimator.

BRIEF DESCRIPTION OF THE DRAWINGS

Other features and advantages of the invention follow from the description hereinbelow, in which exemplary embodiments are explained individually by means of the drawing, in which

FIG. 4 shows an exemplary embodiment of a device according to the invention, with variable mechanical window;

FIG. 5 shows an example of a modular-type collimator in sectional view;

FIG. 6 shows another exemplary embodiment of a mechanical window provided or providable according to the invention;

FIG. 7 shows a differently modified exemplary embodiment of a mechanical window according to the invention, wherein the "principle of distributed holes" is implemented;

FIG. 5 or 6 is sued and, on the other hand, the situation when the invention is not used.

DETAILED DESCRIPTION OF THE INVENTION

The shape and size of a gamma camera's field of view 1 differ with different manufacturers. Square, hexagonal and circular are usual. However, other shapes are also possible. The camera's field of view 1 is generally smaller than the crystal in order to preclude imaging errors in the edge region. The collimator consists of a shielding edge and of the collimating region having the shape and size of the camera's field of view 1. Edge and collimating region can form a unit into which collimating inserts are placed as needed. The collimating region usually has the structure of a honeycomb, with no top or bottom. The walls between the empty holes consist of shielding material, usually lead. Approximately only the radiation incident along the holes' longitudinal axis can pass through the collimator. An object radiating in all directions is therefore imaged in one projection. With parallel-hole collimators, the imageable object size is equal to the size of the camera's field of view.

Modern large-field cameras have a field of view with an inscribed-circle diameter of ca. 35–40 cm.

Figure 1:
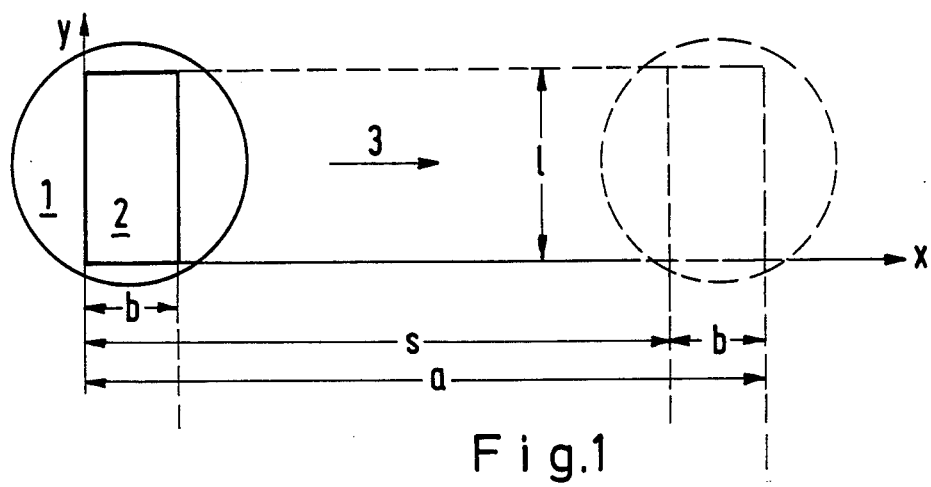
FIG. 1 shows the imaging principle of a gamma camera with a whole-body capability and with rectangular whole-body measuring field for one path.
Figure 2:
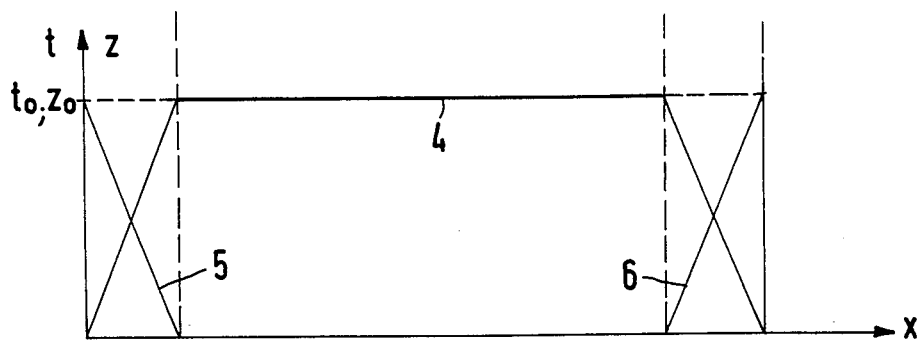
FIG. 2 shows the shape of an imaging curve for a gamma camera with a whole-body capability.

Because of the relative linear motion between camera and object, the whole-body scintigraphy the depictable object size is enlarged to a multiple of the camera's field of view, to ca. 65 cm×200 cm, depending on the manufacturer. FIG. 1 shows the principle of the scanning of a measuring path with a conventional gamma camera with whole-body attachment for a path 1×a. The imageable length a is larger than the scan distance s of the camera. For whole-body photographs the whole-body measuring field 2 of the cameras with whole-body attachment usually does not coincide with the camera's entire field of view 1, but rather is limited electronically to a rectangular window 2 of size b×1. Given a constant scanning speed v of the camera between the start at $x=0$ and the end of the scan at $x=s$, for the dwell time $t(x, y)$ of all object points with $y=$ constant one gets the trapezoidal variation 4 with the height $t_o$ shown in FIG. 2. Given a homogeneous source, one gets the same trapezoidal variation 4 with the height $z_o$ for the number of pulses z as a function of x.

Regardless of the shape of the measuring field, if $b=b(y)$, then $t_o(y)=v \cdot b(y)$. Because of the trapezoidal shape 4 for $t(x,y)$, the starting region $0 \leq x < b$ and the end region $s < x \leq a$ of the imageable regions a·l are not correctly imaged. To compensate for this error, before and after each camera scan the whole-body measuring field 2, at scanning speed v with stationary camera, is in addition electronically scanned opened and closed so that, at the start and end of the path, one gets the additional dwell times 5 and 6 of the object points in the whole-body measuring field 2. The addition of the dwell times 4, 5 and 6 yields a constant dwell time $t_o(x,Y)$ in the measuring field for all object points having the same ordinate y. For nonrectangular measuring fields, the correct imaging of the object requires further corrective measures in order to compensate for unequal dwell times of the object points in the whole-body measuring field. If a constant scanning speed v cannot be assumed because of the acceleration at the beginning and/or the braking at the end, then the shapes of the curves 4, 5 and 6 change. The principle still holds, however.

Regardless of the shape, position and size of the whole-body measuring field 2, which the camera electronically blanks out of its field of view 1, the camera's entire field of view 1 is irradiated by the object, and all the radiation, which interacts with the crystal, must be processed by the camera, even though only part of it is used for the whole-body image.

Owing to "pile-ups" and dead-time effects, counting-rate errors, which cause an erroneous depiction of the distribution of radioactive substances, occur in both types of device. The errors increase concurrently with the counting rate.

Figure 3:
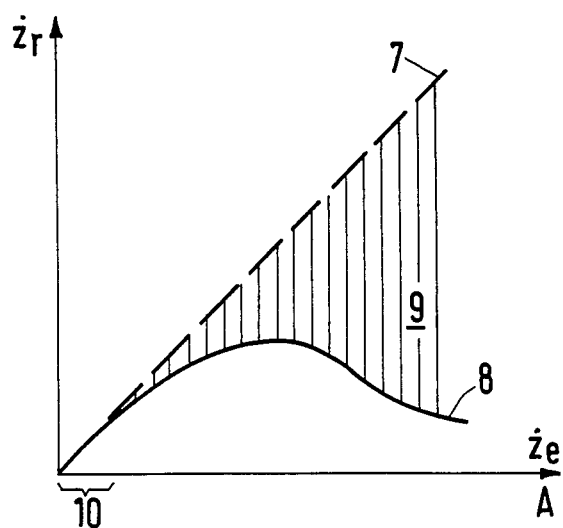
FIG. 3 shows the typical basic relationship between expected counting rate or activity and actual counting rate for gamma-camera photographs.

FIG. 3 shows the typical basic relationship between expected counting rate $z_e$, or activity A, on the abscissa and real counting rate $z_r$ on the ordinate. The dashed line 7 represents the ideal curve without counting-rate error: $z_r = z_e$. The solid curve 8 gives the real variation of a camera's counting rate As the counting rate increases, its slope decreases until it passes through a maximum and then drops off again. The counting-rate error is indicated by the vertical hatching 9. As seen from FIG. 3, for high activities A or for high expected counting rates $z_e$ it may be larger than the measured counting rate $z_r$. The counting-rate errors are not affected by the whole-body measuring field. Both types of device (gamma camera and scanner) are so designed that they operate in the lower range of counting rates, so that the counting-rate errors remain negligibly small for the diagnostic doses 10 customary in nuclear medicine.

However, in order to obtain adequate statistical reliability in reasonable measuring times, the counting rate too should not be arbitrarily small.

In nuclear-medicine therapy, nuclides are administered in many times the diagnostic dose.

In whole-body photographs of these therapy patients, the expected counting rate lies in the upper range of counting rates in FIG. 3, or even outside the depicted range. This results in inadmissibly high counting-rate errors. These are position-dependent with respect to the camera's field of view 1. If the nuclide is unevenly distributed in the object, then they are also position-dependent with respect to the object. This is generally the case in humans because of the organ-specific distribution of the nuclide. The errors cannot be corrected. Hence quantitative information concerning the nuclide distribution in the patient for therapeutic monitoring and for estimating the radiation exposure cannot be reliably obtained from photographs of therapy patients.

The problem underlying the invention is to produce photographs of the distribution of the radioactive substance in a body at high activities, especially in therapy patients, photographs from which more-exact quantitative information than heretofore about the nuclide distribution can be acquired.

Figure 8:
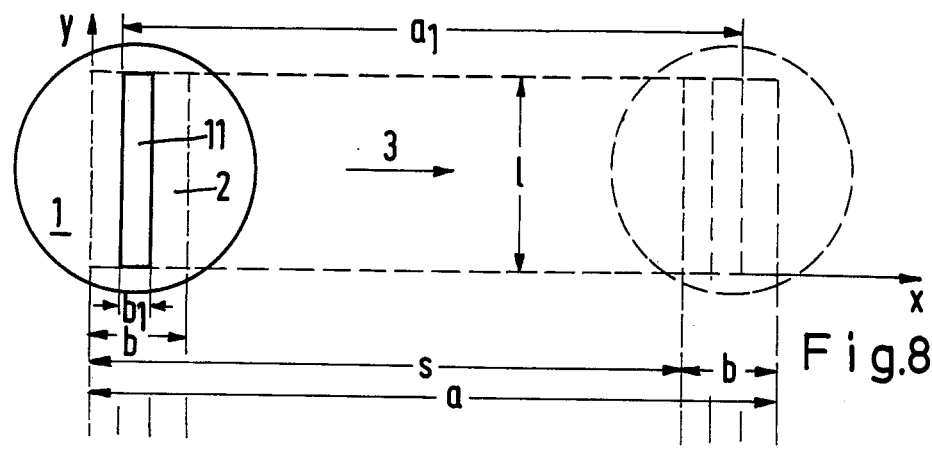
FIG. 8 shows the comparison between, on the one hand, the measurable radiation when the mechanical window per

This problem is solved with the invention through the fact that the radiation incident upon the camera or scanner is diminished by additional shielding of the crystal to such an extent that the counting-rate errors, such as those tolerable in diagnostics, become small. The camera's field of view 1 and, if necessary, also the whole-body measuring field 2 are restricted by a mechanical window 11 or a mechanical diaphragm. This is shown by way of example in FIG. 8 for a rectangular whole-body measuring field 2 and mechanical window 11. The size of this mechanical window 11 determines the fraction of the radiation incident upon the crystal and therewith the counting-rate behavior of the camera. If the incident radiation is homogenous, then the relationship between the size of the mechanical window 11 and the expected counting rate is approximately linear. The shortening of the imageable length a to $a_1$ due to the mechanical window 11 can be offset by setting an adequate scan distance s.

Because of the physical and biological half-life of the nuclide, the activity to be imaged drops in the course of the therapy into the diagnostic range.

To be able to span the entire bandwidth between the initial and final activity, different sizes of the mechanical window 11 are needed.

For producing the mechanical window 11, regardless of the shape, there exist various basic principles, which can be combined with one another.

1. Additional partial shielding of the crystal by additional shielding material between object and collimator and/or between collimator and crystal, e.g., with one or more parts made of heavy metal or alloys thereof, especially lead, bismuth and/or tungsten. This measure involves little expense, and the counting rate of the camera can be lowered into the admissible range. It becomes possible to obtain more-exact information than heretofore concerning nuclide distribution for high activities and the course of therapy.

The needed different window sizes can be attained in different ways:

1.1 Several shields with mechanical windows 11 of different sizes.

1.2 One shield with adjustable mechanical window 11. If the whole-body measuring field 2 is rectangular, that can be achieved most simply by means of two shielding plates that can be moved toward each other, with a variable separation $b_1$. If, moreover, the camera is operated in the undertable mode, then is suffices to place two plates or packages of plates made of shielding material onto the sensor head of the camera in such a way that the incident radiation reaches the camera's field of view 1 only through a slit of width $b_1$.

1.3 The partial shield is assembled from a modular system in such a way that the specific required mechanical window remains free.

The additionally occurring scattered radiation and the reduction of the resolution that occurs because of the widening of the gap between patient and camera can be circumvented through the second possibility:

2. The mechanical window 11 is integrated into the collimator. The collimating region of the collimator acquires the position, size and shape of the mechanical window 11, so that the collimator allows radiation to pass through only in the part of the camera's field of view 1 that corresponds to the mechanical window 11, while shielding against the radiation as completely as possible in the other part. The shape of the mechanical window need not be rectangular. The need different window sizes can be obtained in different ways:

2.1 Several collimators with different mechanical windows. This method is presented for scanner collimators or for camera collimators that are inserted into a holder.

2.2 One collimator with adjustable mechanical window 11. This can be realized, for example, as a comb-like structure, as illustrated in the cutaway view in FIG. 4. Here the combs are shifted toward one another by a suitable mechanism, whereby the hole size and the effective size of the mechanical window 11 can be varied.

2.3 The collimator or parts thereof are assembled on the modular principle from shielding and collimating parts. FIG. 5 shows a cross-section through one possible example. The choice of the part or parts with the collimating mechanical window 11 determines the effective size of the window.

2.4 Despite the mechanical window, for very high activities counting-rate errors can still occur owing to "pile-ups" in the window. These can be reduced by dividing the mechanical window 11 into several subwindows, or by having the holes of the collimating mechanical window, which usually lie as close together as possible, suitably distributed in the collimator or a part thereof, i.e., with separations larger than those necessary for collimation. The result of this is that, from strongly radiating regions, a smaller fraction of the radiation hits the crystal per unit time than would be the case with a continuous mechanical window, as shown in the cutaway drawings in FIGS. 6 and 7. The irregular FIGS. 16 represents the strongly radiating region of the object when the distribution of the activity is nonuniform. The hatch subareas designate the fraction radiating into the camera, a fraction which for the distributed holes of FIG. 7 is smaller than for the continuous collimating region of FIG. 6.

The distribution of the hole must be such that all object points are covered uniformly during the camera scan. That can be done, for example, by arranging the holes in rows which, as in FIG. 7, form an angle $\alpha$ not equal to 0° with the scan direction 3. In scan direction 3, several holes may lie one behind another, depending on the required effective window-size.

If the collimator is constructed of several parts, then the separation surfaces between the individual parts must be so fashioned that the shielding is guaranteed. This can be achieved by proper shaping of the separation surfaces, as seen from FIG. 5.

Figure 9A:
FIG. 9 shows the dwell times of the object points in the partially shielded whole-body measuring field per FIG. 8 for starting, middle and end regions of imaging paths.
Figure 9B:
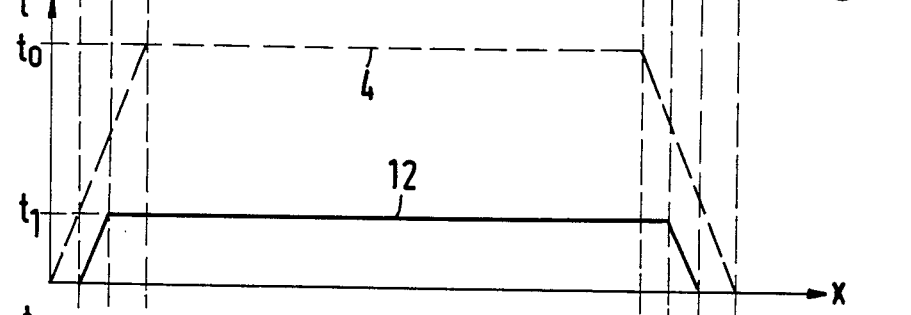
Figure 9C:
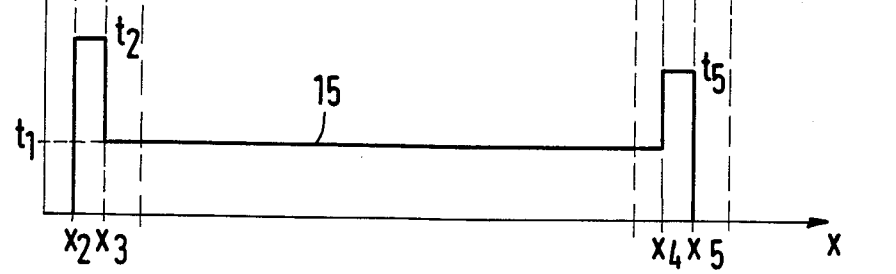

If the mechanical window 11 covers the camera's whole-body measuring field 2, then different dwell times $t(x,y)$ of the object points in the measuring field 2 are obtained for the starting, middle and end regions. By way of example, this is illustrated in FIG. 9 for a rectangular electronic measuring field 2 and mechanical window 11 per FIG. 8.

For the scanning phase of the photograph with the speed $v=$ constant, one finds for the dwell time $t(x,y)$ the trapezoidal curve 12 with the height $t_1(y)=v \cdot b_1(Y)$. If not only the camera's field of view 1 but also the whole-body measuring field 2 are restricted, then for unchanged scanning speed $v$ one gets $t_1 < t_o$ because $v = t_o/b = t_1/b_1$, as illustrated in FIG. 9. For unchanged open and closed scanning of the electronic window, one gets the curve 13 at the start of the path and the curve 14 at the end. In all, for one camera scan one gets the curve 15 with $t_2$ at the start, $t_1$ in the middle and $t_5$ at the end. When the mechanical window 11 is positioned at the center of the whole-body measuring field 2, $t_2$ becomes equal to $t_5$. When the mechanical window 11 is positioned at the edge of the whole-body measuring field 2, the error occurs only on one side.

Imaging errors occur because of the erroneous dwell times $t_2$ and $t_5$. Regardless of the window shape, these can be corrected or circumvented in the following ways:

1. Adaptation of the electronic whole-body measuring field 2 to the mechanical window 1 in size, position and shape, so that the mechanical window does not cover the electronic whole-body measuring field 2.

2. The starting and end regions are not used to construct the image, so that only the region with $t(x,y)=t_1(y)$ has an effect. The camera's scanning distance s is chosen sufficiently long.

3. The error depends only on the window geometries and can be corrected electronically or by computer while the photograph is being taken or afterwards. For a continuous mechanical window 11, the number of pulses at the start and end of the path are corrected in accordance with the dwell times as follows:

$$t_1 = t_2 - t_3 \text{ for } x_2 \leq x \leq x_3$$

and $$t_1 = t_5 - t_4 \text{ for } x_4 \leq x \leq x_5,$$

respectively. For a divided mechanical window 11, suitable allowance must be made for this division.

The features of the invention disclosed in the above description, in the drawings and in the claims may be essential, both individually or in any combination, for realization of the invention in different embodiments.

I claim:

1. A process for depicting the distribution of high activities of radioactive substances by means of a whole-body scintigraphic device having a camera means which detects radiation emitted by a radioactive substance, comprising partially shielding said device from said radiation as a function of radiation intensity in order to optimize the counting rate.

2. The process as claimed in claim 1, wherein the scintigraphic device comprises a collimator.

3. The process as claimed in claim 2, wherein the whole-body scintigraphic device further comprises a multihole collimator.

4. The process as claimed in claim 3, wherein partial shielding is provided by the multihole collimator.

5. The process as claimed in claim 2
wherein the collimating region of the collimator is reduced in size in order to diminish the incident radiation.

6. The process as claimed in claims 1 or 2, in which the camera means comprises a camera having a whole-body measuring field and a mechanical window, wherein the whole-body measuring field is adapted in shape, size and/or position to the mechanical window.

7. The process as claimed in claim 1, or 2, in which the camera means comprises a camera having a whole-body measuring field and a mechanical window, wherein only the part of the imageable region in which the dwell time of object points is constant is used to construct the image.

8. The process as claimed in claim 1, 24, 25, 4, or 20, in which the camera means comprises a camera having a whole-body measuring field and a mechanical window, wherein at the start and end of each imaging path the numbers of pulses are corrected in accordance with the dwell times of object points in the whole-body field.

9. An apparatus for depicting the distribution of high activities of radioactive substances by means of a whole-body scintigraphic device comprising a camera means for detecting radiation emitted by a radioactive substance, and means for partially shielding said device from said radiation as a function of radiation intensity in order to optimize the counting rate.

10. An apparatus as claimed in claim 9, wherein the camera means comprises a camera having a camera field of view, a whole-body measuring field and a mechanical window wherein the camera field of view and/or the whole-body measuring field is partially shieldable by the mechanical window.

11. An apparatus as claimed in claim 10, wherein the mechanical window has holes formed therein which are distributed over the entire wholebody measuring field or a part of said whole-body measuring field.

12. An apparatus as claimed in claim 10 wherein said mechanical window has a continuous structure.

13. An apparatus as claimed in claim 10, wherein the mechanical window is continuously variable in size.

14. An apparatus as claimed in claim 10, wherein the scintigraphic device further comprises a collimator.

15. An apparatus as claimed in 14 wherein said mechanical window is integrated into said collimator by shape, size and position of the collimating region, and the region of the radiation lying outside the mechanical window is largely shielded against.

16. An apparatus as claimed in claim 14, wherein the collimator comprises a plurality of parts assembled to provide a mechanical window wherein the size of said mechanical window is determined by the choice of the part or parts.

17. An apparatus as claimed in claim 9, wherein the scintigraphic device comprises a collimator.

18. An apparatus as claimed in claim 17, wherein the means for partially shielding the device are provided in addition to the collimator.

19. An apparatus as claimed in claim 17, wherein the collimator comprises a multihole collimator and one or more of the holes of the collimator are shieldable to provide said means for partially shielding.

20. An apparatus as claimed in claim 9, wherein the camera means comprises a camera having a camera field of view, a wholebody measuring field and a plurality of mechanical windows of different sizes, wherein the camera field of view and/or the whole-body measuring field is partially shieldable by one of the mechanical windows

* * * * *